(12) United States Patent
Baldwin

(10) Patent No.: US 6,870,949 B2
(45) Date of Patent: Mar. 22, 2005

(54) COAXIAL NARROW ANGLE DARK FIELD LIGHTING

(75) Inventor: Leo Baldwin, Beaverton, OR (US)

(73) Assignee: Electro Scientific Industries, Portland, OR (US)

( * ) Notice: Subject to any disclaimer, the term of this patent is extended or adjusted under 35 U.S.C. 154(b) by 146 days.

(21) Appl. No.: 10/373,934

(22) Filed: Feb. 26, 2003

(65) Prior Publication Data

US 2004/0165759 A1 Aug. 26, 2004

(51) Int. Cl.$^7$ ................................................. G06K 9/00
(52) U.S. Cl. .................... 382/145; 382/141; 356/237.3; 356/237.4; 356/600; 356/446
(58) Field of Search ......................... 382/141, 144–147, 382/149, 203; 356/237.2, 237.3, 237.4, 237.5, 237.6, 336, 609, 401, 446, 600; 348/125, 86; 250/227.29, 227.3, 227.31; 359/436, 385

(56) References Cited

U.S. PATENT DOCUMENTS

| | | | |
|---|---|---|---|
| 5,231,536 A | | 7/1993 | Wilt et al. |
| 5,377,001 A | * | 12/1994 | Malin et al. .............. 356/237.2 |
| 5,469,294 A | | 11/1995 | Wilt et al. |
| 5,737,122 A | * | 4/1998 | Wilt et al. .................. 359/436 |
| 6,445,812 B1 | | 9/2002 | Lai et al. |
| 2002/0009218 A1 | | 1/2002 | Chapman et al. |
| 2002/0037105 A1 | | 3/2002 | Michael |
| 2002/0113970 A1 | | 8/2002 | Baldwin et al. |
| 2003/0009242 A1 | | 1/2003 | Bocchi |
| 2003/0025918 A1 | * | 2/2003 | Watkins et al. ............. 356/609 |
| 2003/0202178 A1 | * | 10/2003 | Tsuji et al. .............. 356/237.2 |

* cited by examiner

Primary Examiner—Bhavesh M. Mehta
Assistant Examiner—Ali Bayat
(74) Attorney, Agent, or Firm—Young & Basile, P.C.

(57) ABSTRACT

A coaxial narrow angle dark field imaging system is provided. The system utilizes a telecentric lens to illuminate objects with symmetric coaxial narrow angle dark field illumination. The illumination technique is particularly suited to highlight minor features or defects on planar specular objects. In particular, the coaxial light source directs light rays towards a telecentric lens which redirects the light rays towards the substantially planar specular object. The light rays are reflected back through the telecentric lens towards a camera. To the extent that the light rays are reflected from a planar specular portion of the object the light rays are blocked by a telecentric stop. Light rays reflected from a defect or feature in the planar specular object will pass through an aperture in the stop to a camera.

16 Claims, 4 Drawing Sheets

COAXIAL NARROW ANGLE DARK FIELD LIGHTING

FIELD OF THE INVENTION

The present invention relates to imaging optics and associated illumination systems and in particular to an apparatus which provides coaxial narrow angle dark field illumination of a planar specular object having at least one defect.

BACKGROUND OF THE INVENTION

There is a class of semiconductor products that are predominantly planar and specular (flat and shiny) and it is frequently necessary to image these devices in such way that even minor deviations from planar and specular are imaged with adequate contrast. One such class of products are semiconductor wafers which may be provided with indicia that indicate, among other things, wafer number and manufacturer. These indicia are defects in the surface of the wafer and are typically a matrix of laser etched pits. These indicia are known in the art as "soft marks". It is necessary to image these marks to read the codes at various steps along the manufacturing process.

After the devices have been singulated (generally cut by saw into individual rectangular devices), it may be necessary to inspect the edges for small chips and cracks that may propagate over time and cause premature device failure. These inspection processes are automated and use electronic imaging cameras in combination with digital electronic computers that are programmed to perform the necessary inspections, measurements and identifications.

Dark field lighting, in general, is a technique well known to those skilled in the art and is particularly useful to inspect defects on specular objects. The definition of dark field lighting is dependant upon the properties of the illumination source, its position relative to both the object and the observer, or camera, and on the properties of the object being illuminated. In order to meet the definition of dark field lighting, it is necessary that the majority of the illumination incident on the object is reflected in a direction or directions that do not enter the optical aperture of the observer or camera. Dark field illumination can be compared against bright field illumination where the majority of light is reflected directly into the camera.

With reference to FIG. 1, dark field lighting can be achieved by placing the light source such that it is pointing at the object at an angle to the line between the camera and the object. This angle has to be greater that the angle over which the object will diffuse light. If the object has a generally diffuse reflective nature, then the angle must be larger than the half-angle over which the object will distribute incident illumination by diffuse reflection. If the object is specular, that is if the object diffuses incident illumination over a small angle or with very low efficiency or both, then the angle may be very small.

It may be desirable to make the illumination source symmetric. In this case the source may be manufactured in an annular shape and placed coaxial to the optical axis, or a plurality of sources may be arranged in an annular shape. The diameter of this annulus and its proximity to the object determine the range of angles over which the illumination is incident upon the object. Such lights are known to those skilled in the art as ring lights and are variously configured to be "high angle" or "low angle."

In imaging certain objects, it is desirable to highlight very minor features in a surface which is otherwise substantially planar and specular. These include soft marks and the edges of singulated devices. To achieve this, it is necessary to bring the illumination source as nearly on-axis with the imaging system as possible without causing the illumination source to be directly reflected into the imaging system, i.e., narrow angle. The most effective way to achieve this, as currently know, is with the aid of baffles and providing a particular alignment between the illumination source, the object, the baffles, and the imaging system.

An implementation of this can be seen in commonly assigned U.S. Pat. No. 5,737,122 entitled Illumination System for OCR Of Indicia on A Substrate (hereinafter the '122 patent). An illustration of one embodiment of the '122 patent is shown at FIG. 2. The '122 patent describes that the axis of the camera and the axis of the lighting module are at complimentary acute angles symmetric about the normal to a specular object. The narrow-angle dark field lights are positioned close to the optical axis and are prevented from being directly imaged by the camera by baffles placed in the imaging path to prevent this. The position of the baffles restricts the field of view of the imager, but this is considered an acceptable compromise. In these designs, the narrow angle dark field lighting is composed of two opposed banks and has only one-fold symmetry. When imaging generally circular pits on wafers that make up the symbology of the lot code or serial number, this one-fold symmetry can result in a degraded image.

SUMMARY OF THE INVENTION

The present invention provides an imaging system for imaging a defect on a planar specular object. The system includes a telecentric lens having a defined axis and focal point. The telecentric lens is operative to provide an image of the object to a camera. A source of illumination is positioned to illuminate the object along the axis of the telecentric lens. For a specular object a telecentric stop which includes an aperture therein blocks light reflected from the planar specular object while allowing light reflected from the defect to pass through the aperture.

According to another aspect of the invention a beam splitter is provided such that the source of illumination may be positioned normal to the axis of the telecentric lens.

According to another aspect of the invention the aperture of the telecentric stop is positioned proximate to the focal point of the telecentric lens.

According to another aspect of the invention a rear lens group is provided which focuses the image of the defect onto the camera.

According to another aspect of the invention the source of illumination comprises a circular group of LEDs.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 5 is a plan view of a light source used in accord with the present invention.

DETAILED DESCRIPTION OF THE PREFERRED EMBODIMENTS

The present invention addresses the requirement to illuminate and form an image of a predominantly planar and specular surface such that the deviations from planarity or specularity of the object being imaged are reproduced with enhanced contrast. The embodiments of the present invention, as described below, utilize a telecentric lens to illuminate objects with symmetric coaxial narrow angle dark field illumination. This illumination technique is particularly suited to highlighting minor features or defects on planar specular objects. Specific examples of such objects include silicon wafers while the defects may include soft mark symbols on silicon wafers and/or edge irregularities on chip scale devices.

In particular a light source provides annular cones of light rays toward a telecentric lens. The telecentric lens redirects the light rays toward a substantially planar specular object such that the light rays are parallel and normal to the object. A property of the planar specular object is to reflect light at an angle complementary to the incident angle, in this case normal to the surface of the object. Upon reflection, the light rays are coined image rays. The image rays will be retroreflected from a substantially planar specular object and inversely transformed through the telecentric lens to the point at which they originated. The system provides a telecentric stop, with a central aperture coincident with the light source such that substantially no light passes through to a camera. However, if there is a defect in the specular surface, the light will be disturbed and it is probable that some portion of the light will pass through the aperture of the telecentric stop and onto a camera.

Figure 1:
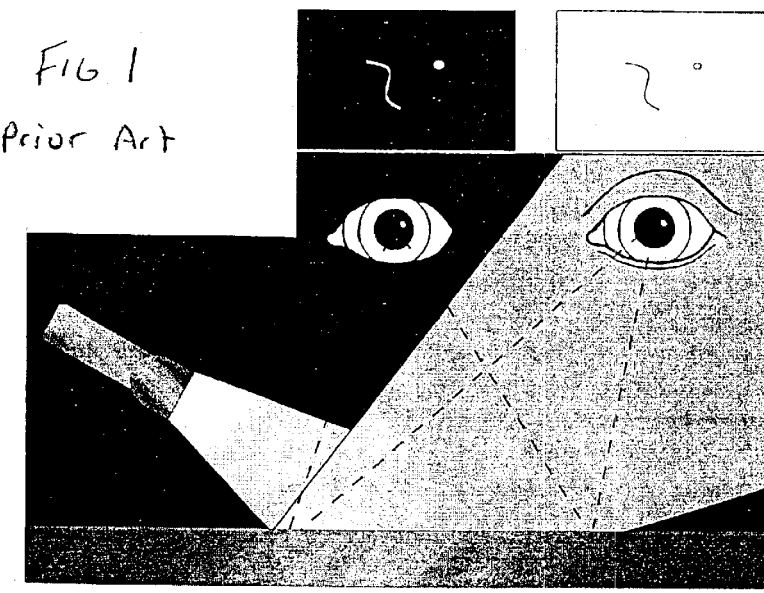
FIG. 1 is a generic representation illustrating the concept of dark field illumination.
Figure 2:
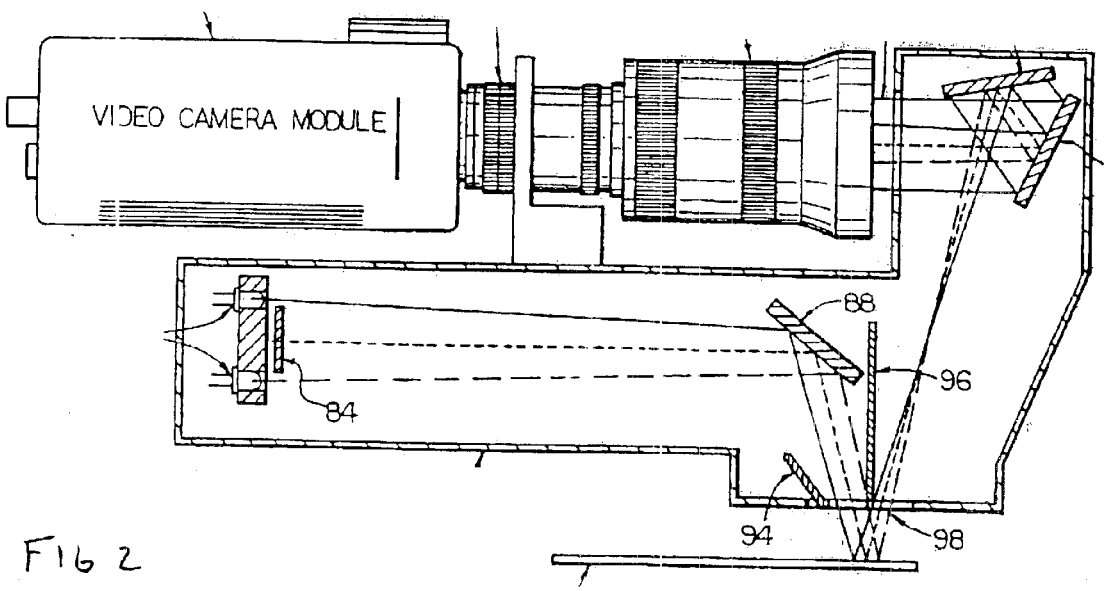
FIG. 2 is an illustration of a prior art illumination system including baffles.
Figure 3:
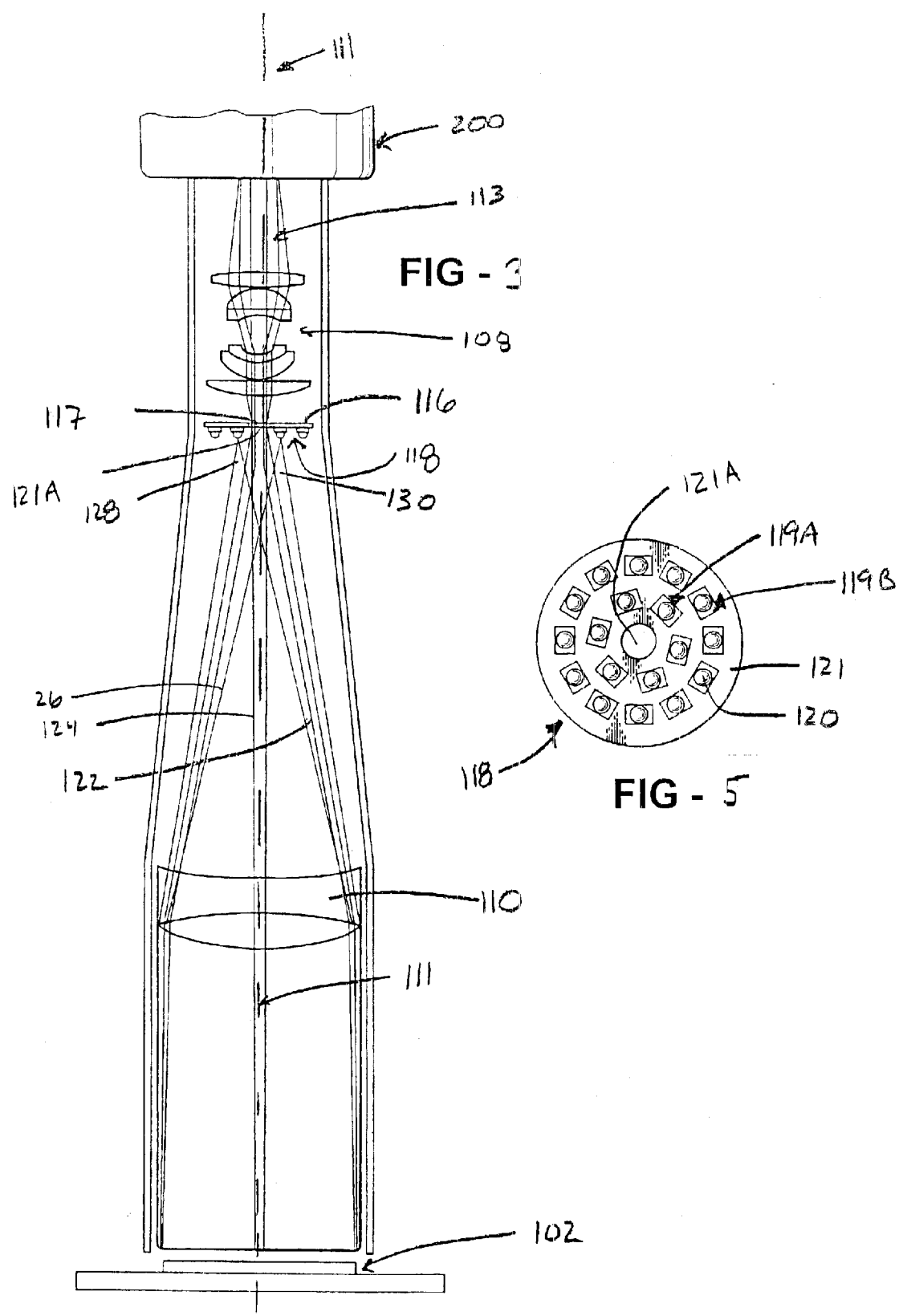
FIG. 3 is a partially pictorial, partially sectional diagram illustrating a first preferred embodiment in accord with the present invention.
Figure 4:
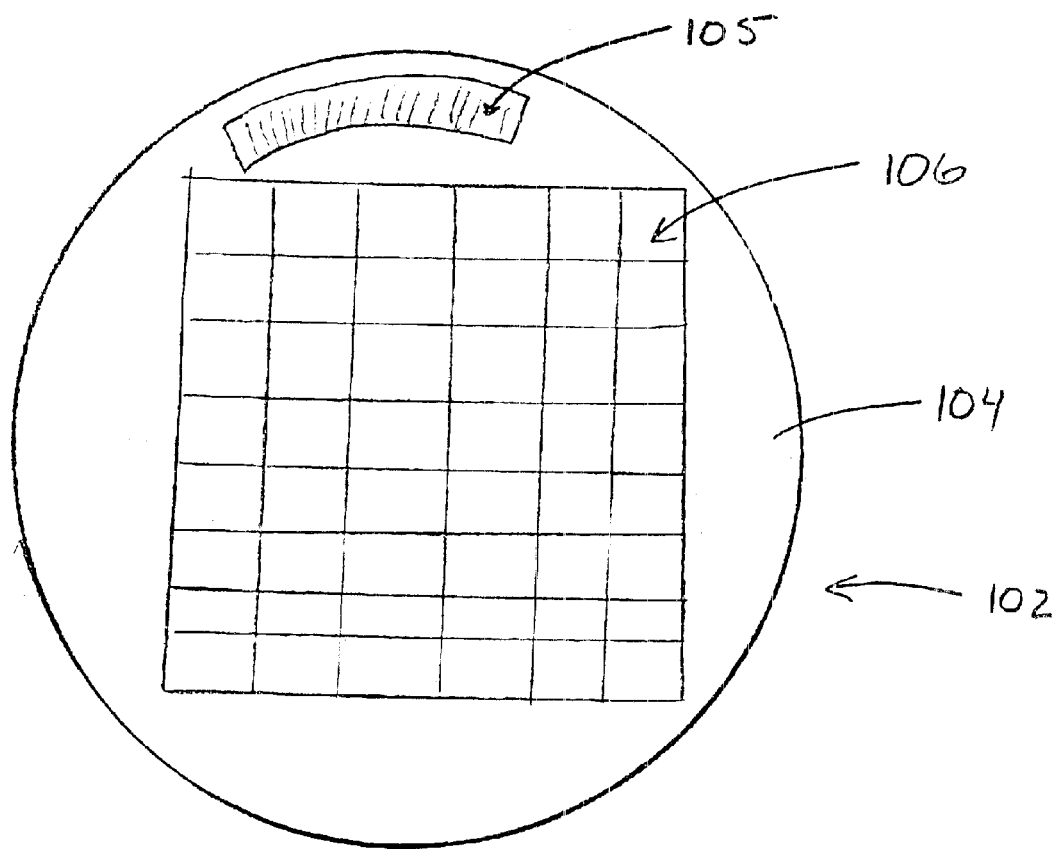
FIG. 4 is an illustration of a silicon wafer including a soft mark.

With reference to the FIG. 3 there is shown a partially pictorial, partially sectional diagram of the first preferred optical imaging system 100 in accord with the present invention. FIG. 3 illustrates a planar object 102. Planar object 102 is preferably a silicon wafer 104 which is illustrated in more detail in FIG. 4. Silicon wafer 104 is specular in nature. Silicon wafer 104 typically includes defects such as a soft mark 105. Soft mark 105 is made up of a collection of laser etched pits and provide information regarding silicon wafer 104. Silicon wafer 104 also includes a plurality of semiconductor devices 106. While the present invention is described in terms of inspecting silicon wafer 104 and in particular imaging soft mark 105 it is understood that the present invention has equal applicability to imaging other planar objects. For example, when semiconductor devices 106 are singulated they may be inspected for edge defects.

With continued reference to FIG. 3 optical imaging system 100 includes a pair of lens groups coined a rear group 108 and a telecentric field lens 110 respectively. One source of appropriate lenses for both rear lens group 108 and telecentric field lens 110 is Edmund Scientific. Rear lens group 108 and telecentric field lens 110 operate together to direct an image 113 of softmark 105 to a camera 200 as will be described in greater detail below. Camera 200 is preferably a digital camera including a CCD or CMOS type sensor.

Rear lens group 108 is defined by a collection of corrected objective lenses and includes an entrance pupil 109. Rear lens group 108 is preferably low in distortion and has sufficient resolving power to complement camera 200. It is understood that rear lens group 108 may be different depending upon what type of camera 200 is used.

It is understood that telecentric field lens 110 operates as a telecentric field lens to render the imaging of the object telecentric along the plane of object 102. Put another way, light rays are parallel to one another as they exit telecentric lens 110 and are preferably normal to the plane of object 102. When illuminated by a light source 118 it is understood that telecentric lens 110 and lens group 108 operate to form an image 113 at camera 200. Telecentric lens 110 has a number of defining characteristics including an axis 111 and a telecentric aperture or focal point 112. As illustrated in FIG. 3 focal point 112 of telecentric field lens 110 is coincident with entrance pupil 109 of rear lens group 108. Axis 111 defines the optical axis for system 100 such that rear lens 108 and camera are similarly positioned along axis 111.

An illumination source 118 is also provided. Illumination source 118 is positioned to provide narrow angle lighting which is coaxial with the axis 111 of telecentric field lens 110. FIG. 3 illustrates the first preferred positioning of light source 118 physically along axis 111. It is understood, and as described below, that light source 118 can be positioned physically remote from axis 111 in an optically equivalent manner.

A telecentric stop 116 is positioned between rear lens group 108 and telecentric field lens 110 and is centered on axis 111 of telecentric field lens 110. Telecentric stop 116 is preferably placed proximate entrance pupil 109 of rear lens group 108. Telecentric stop 116 is preferably a physical optical stop which includes a central aperture 117. Aperture 117 is also positioned proximate to the focal point 112 of telecentric lens 110.

The preferred illumination source is illustrated in FIG. 5. With reference to FIG. 5 there is shown an annular light source utilizing a plurality of LEDs 120 mounted to a printed circuit board 121. It is understood that printed circuit board 121 may function as the telecentric stop 116. Printed circuit board 121 includes an aperture 121A which is at least as large as aperture 117 of telecentric stop 116. In the event that an iris diaphragm aperture is used together with telecentric stop 116, aperture 121A must be as large as the largest aperture setting available. As shown LEDs 120 are organized into an inner circular group 119A and an outer circular group 119B. It is understood that inner group 119A and outer group 119B provide slightly different narrow angle lighting of object 102. Inner and outer groups 119A, 119B may be illuminated together or in the alternate, depending upon the qualities of object 102. It is understood additional circular groups of LEDs could be provided.

The sensitivity of the system to the type of defect is principally determined by the focal ratio between telecentric lens 110 and the diameter of the light source. The present invention provides a way to adjust this sensitivity. In particular, the different diameters of annular light sources 119A and 119B may be used or alternately the diameter of aperture 117 of telecentric stop 116 may be adjusted. Aperture 117 may be adjustable through the use of an iris diaphragm thereby providing an adjustable focal ratio for the system.

Figure 6:
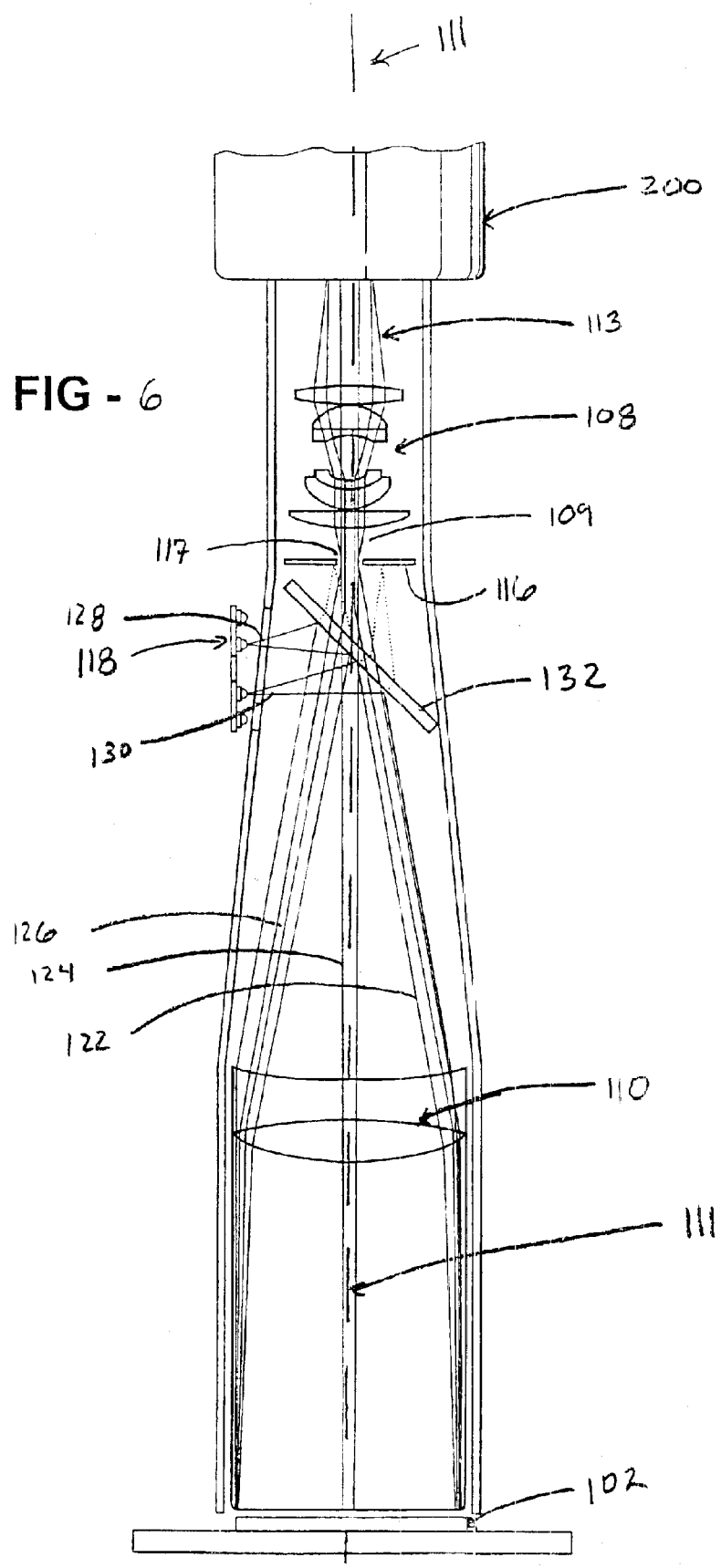
FIG. 6 is a partially pictorial, partially sectional diagram illustrating a second preferred embodiment in accord with the present invention.

FIG. 6 illustrates a second preferred embodiment which is optically equivalent to the embodiment shown in FIG. 3. As illustrated in FIG. 6, the second preferred embodiment includes a partially reflective mirror or beam splitter 132 positioned along axis 111 of telecentric field lens 110. Beam splitter 132 allows light source 118 to be positioned normal to axis 111 of telecentric field lens 110. In the second preferred embodiment light source 118 is positioned at an optically equivalent location to that of telecentric stop 116.

With reference again to FIG. 3 light source 118 causes light rays 128 and 130 to project toward telecentric field lens 110 such that rays 128 and 130 are focused proximate to object 102 and are substantially parallel. It is understood that light rays 128 and 130 are projected as annular cones which become parallel as they pass through telecentric lens 110. Light rays are reflected from object 102 as image forming rays 122, 124 and 126. In the event that light rays 128 and 130 reflect from a specular portion of object 102 image forming rays 122 and 126 will strike telecentric stop 116 and not enter lens group 108. In particular image rays 122 and 126 will be retro reflected from a substantially planar a specular surface to create annular cones of illumination which will return to their point of origin as a mirror image. However, when light rays 128 and/or 130 are reflected from a defect, image forming rays 124 will pass through aperture 117 in telecentric stop 116, be focused by lens group 108, and form an image 113 at camera 200.

With reference to the second preferred embodiment in FIG. 6, the system operates in a manner equivalent to that above described save for the beam splitter 132. In particular, beam splitter 132 functions to reduce the intensity of light which may ultimately pass through aperture 117 of telecentric stop 116.

The present invention has significant advantages over the prior art. Namely, the angle between the optical axis and the narrow angle dark field lighting can be arbitrarily small to the point of becoming bright field lighting if desired. Further the sensitivity of the system can be adjusted as above described by selecting different diameter of lighting or by adjusting the aperture of the telecentric stop. Further, the full field of view of the camera can be used because the system eliminates baffles which were required in the prior art. The system also provides full circular symmetry over the entire field of view.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An imaging system for imaging a defect on a planar specular object comprising:
   a telecentric lens having a defined axis and focal point, the telecentric lens operative to provide an image of the object to a camera;
   a source of illuminaton positioned to illuminate the object along the axis of the telecentric lens; and
   a telecentric stop including an aperture therein positioned to block light reflected from the planar specular object while allowing light reflected from the defect to pass through the aperture.

2. An imaging system as in claim 1 wherein the defect is a soft mark.

3. An imaging system as in claim 1 further comprising a second lens group having an entrance pupil positioned between the telecentric stop and the camera.

4. An imaging system as in claim 3 wherein the focal point of the telecentric lens is coincident with the entrance pupil of the second lens group.

5. An imaging system as in claim 4 wherein the source of illumination comprises at least one generally circular group of luminous elements.

6. An imaging system as in claim 5 wherein the telecentric stop is in close proximity to the circular group of luminous elements.

7. An imaging system as in claim 4 wherein the source of illumination includes a plurality of concentric generally circular groups of luminous elements.

8. An imaging system as in claim 1 further comprising an iris diaphragm aperture positioned in the aperture of the telecentric stop whereby the focal point of the telecentric lens is adjustable.

9. An imaging system for imaging a defect on a planar specular object comprising:
   a telecentric lens positioned proximate to the object, the telecentric lens having a defined axis and focal point, the telecentric lens operative to provide an image of the object to a camera;
   a beam splitter positioned along the axis of the telecentric lens;
   a source of illumination positioned to normal to the axis of the telecentric lens and positioned to direct a plurality of light rays toward the beam splitter to illuminate the object along the axis of the telecentric lens; and;
   a telecentric stop including an aperture therein, the telecentric stop positioned along the axis of the telecentric lens to block light reflected from the planar specular object while allowing light reflected from the defect to pass through the aperture.

10. An imaging system as in claim 9 wherein the defect is a soft mark.

11. An imaging system as in claim 9 further comprising a second lens group having an entrance pupil positioned between the telecentric stop and the camera.

12. An imaging system as in claim 11 wherein the focal point of the telecentric lens is coincident with the entrance pupil of the second lens group.

13. An imaging system as in claim 11 wherein the source of illumination includes a plurality of concentric generally circular groups of luminous elements.

14. An imaging system as in claim 9 wherein the source of illumination comprises at least one generally circular group of luminous elements.

15. An imaging system as in claim 14 wherein the telecentric stop is in close proximity to the circular group of luminous elements.

16. An imaging system as in claim 9 further comprising an iris diaphragm aperture positioned in the aperture of the telecentric stop whereby the focal ratio of the telecentric lens is adjustable.

* * * * *